United States Patent
Hoffman

(10) Patent No.: US 7,922,748 B2
(45) Date of Patent: Apr. 12, 2011

(54) REMOVABLE POLYAXIAL HOUSING FOR A PEDICLE SCREW

(75) Inventor: Zachary M. Hoffman, Minneapolis, MN (US)

(73) Assignee: Zimmer Spine, Inc., Minneapolis, MN (US)

( * ) Notice: Subject to any disclaimer, the term of this patent is extended or adjusted under 35 U.S.C. 154(b) by 731 days.

(21) Appl. No.: 11/424,562

(22) Filed: Jun. 16, 2006

(65) Prior Publication Data

US 2008/0009862 A1 Jan. 10, 2008

(51) Int. Cl.
*A61B 17/70* (2006.01)
*A61B 17/86* (2006.01)

(52) U.S. Cl. ........ 606/267; 606/264; 606/265; 606/266; 606/269; 606/271; 606/272; 606/300; 606/305; 606/306

(58) Field of Classification Search .......... 606/265–267, 606/269, 271, 272, 300, 305, 306, 264
See application file for complete search history.

(56) References Cited

U.S. PATENT DOCUMENTS

| | | | |
|---|---|---|---|
| 4,887,596 A | 12/1989 | Sherman | |
| 4,946,458 A | 8/1990 | Harms et al. | |
| 5,207,678 A | 5/1993 | Harms et al. | |
| 5,725,528 A | 3/1998 | Errico et al. | |
| 5,735,851 A | 4/1998 | Errico et al. | |
| 5,782,833 A | 7/1998 | Kaider | |
| 5,910,142 A | 6/1999 | Tatar | |
| 5,989,254 A | 11/1999 | Katz | |
| 6,004,322 A | 12/1999 | Bernstein | |
| 6,113,601 A | 9/2000 | Tatar | |
| 6,183,472 B1 | 2/2001 | Lutz | |
| 6,368,321 B1 | 4/2002 | Jackson | |
| 6,371,957 B1 * | 4/2002 | Amrein et al. | 606/272 |
| 6,402,752 B2 | 6/2002 | Schaffler-Wachter et al. | |
| 6,423,064 B1 | 7/2002 | Kluger | |
| 6,482,207 B1 | 11/2002 | Errico | |
| 6,485,494 B1 | 11/2002 | Haider | |
| 6,554,834 B1 | 4/2003 | Crozet et al. | |
| 6,565,567 B1 | 5/2003 | Haider | |
| 6,869,433 B2 | 3/2005 | Glascott | |
| 6,964,666 B2 | 11/2005 | Jackson | |
| 7,686,835 B2 * | 3/2010 | Warnick | 606/264 |
| 2004/0204711 A1 | 10/2004 | Jackson | |
| 2004/0236330 A1 * | 11/2004 | Purcell et al. | 606/61 |
| 2005/0277928 A1 * | 12/2005 | Boschert | 606/61 |
| 2006/0025771 A1 | 2/2006 | Jackson | |
| 2006/0084979 A1 | 4/2006 | Jackson | |
| 2006/0095038 A1 | 5/2006 | Jackson | |
| 2006/0100621 A1 | 5/2006 | Jackson | |
| 2006/0100622 A1 | 5/2006 | Jackson | |

(Continued)

*Primary Examiner* — Thomas C Barrett
*Assistant Examiner* — Sameh Boles
(74) *Attorney, Agent, or Firm* — Seager, Tufte & Wickhem, LLC

(57) ABSTRACT

A polyaxial body is selectively removable from a pedicle screw in a spinal fixation system without disruption of the screw's placement in the patient's spine. The polyaxial body according to various embodiments of this invention may be locked relative to the screw head and coupled to the spine rod without deformation of the screw or body components while still allowing for subsequent removal of the body from the screw head. The head of the pedicle screw is threadably engaged with a retainer ring on the polyaxial body thereby permitting selective removal of the body from the screw head without disrupting the placement of the screw in the spine. This allows for the pedicle screw to remain in the spine as the fixation system is adjusted as required by the surgeon for subsequent and reliable reanimation.

12 Claims, 4 Drawing Sheets

U.S. PATENT DOCUMENTS

| | | |
|---|---|---|
| 2006/0200133 A1 | 9/2006 | Jackson |
| 2006/0200136 A1 | 9/2006 | Jackson |
| 2006/0276789 A1* | 12/2006 | Jackson .......................... 606/61 |
| 2007/0016200 A1 | 1/2007 | Jackson |
| 2007/0055244 A1 | 3/2007 | Jackson |
| 2007/0293862 A1 | 12/2007 | Jackson |
| 2008/0039844 A1 | 2/2008 | Jackson |

* cited by examiner

REMOVABLE POLYAXIAL HOUSING FOR A PEDICLE SCREW

TECHNICAL FIELD

This invention relates generally to spinal fixation devices and more specifically relates to a polyaxial pedicle screw assembly with removable components.

BACKGROUND

The human spinal cord is a highly complex system of bones and connective tissues that provide support for the body and protect the delicate spinal column and nerves. The spinal column includes a series of vertebrae stacked one atop the other. Each vertebral body includes a relatively strong cortical bone portion forming the outside surface of the body and a relatively weak cancellous bone portion forming the center of the body. An intervertebral disc is situated between each vertebral body that provides for cushioning and dampening of compressive forces applied to the spinal column. The vertebral canal containing the delicate spinal cord and nerves is located just posterior to the vertebral bodies.

Various types of spinal column disorders include scoliosis (abnormal lateral curvature of the spine), kyphosis (abnormal forward curvature of the spine, usually in the thoracic spine), excess lordosis (abnormal backward curvature of the spine, usually in the lumbar spine), spondylolisthesis (forward displacement of one vertebra over another, usually in a lumbar or cervical spine). Other disorders are caused by abnormalities, disease or trauma, such as ruptured or slipped discs, degenerative disc disease (DDD), fractured vertebra, and the like. Patients that suffer from such conditions usually experience extreme and debilitating pain as well as diminished nerve function.

One known technique to address many such spinal conditions is commonly referred to as spinal fixation. Surgical implants are used for fusing together and/or mechanically immobilizing adjacent vertebrae of the spine. Spinal fixation may also be used to improve the position of the adjacent vertebrae relative to one another so as to alter the overall alignment of the spine. Such techniques have been used effectively to treat the above-described conditions and, in most cases, to relieve pain suffered by the patient. However, as will be set forth in more detail below, there are some disadvantages associated with current fixation devices.

One particular spinal fixation technique includes immobilizing the spine by using orthopedic rods, commonly referred to as spine rods, which run generally parallel to the spine. This is accomplished by exposing the spine posteriorly and fastening bone screws to the pedicles of the appropriate vertebrae. The pedicle screws are generally placed two per vertebra, one at each pedicle on either side of the spinous process, and serve as anchor points for the spine rods. Clamping elements adapted for receiving a spine rod there through are then used to join the spine rods to the screws. The clamping elements are commonly mounted to the head of the pedicle screws. The aligning influence of the rods forces the spine to conform to a more desirable shape. In certain instances, the spine rods may be bent to achieve the desired curvature of the spinal column.

One type of clamping element mounted to a pedicle screw has a housing resembling a saddle connected to the screw. The housing includes a U-shaped channel for receiving a spine rod therein. After the pedicle screw has been inserted into bone and the spine rod is positioned in the U-shaped channel, a set screw is threaded into internal threads of the housing for securing the spine rod in the U-shaped channel.

Surgeons have frequently encountered considerable difficulty when attempting to insert spinal fixation devices. For example, surgeons frequently are unable to efficiently and adequately place the spine rod into the U-shaped heads of the pedicle bone screws because the U-shaped heads of the screws are often not aligned with one another due to curvature in a spine and the different orientations of the pedicle screws. The spine rods are often bent in multiple planes to couple the pedicle screws to the rod, which may lead to weaker connections with the rod. These problems also result in significantly longer operations, thereby increasing the likelihood of complications associated with surgery.

One known solution to some of these problems is a polyaxial pedicle screw that has a spherically shaped head. The spherically shaped head permits movement of the U-shaped housing or rod clamping assemblies relative to the pedicle screw shaft. While the ability to provide a polyaxial orientation for the pedicle screw connection with the spine rod has offered significant benefits, very often such pedicle screw assemblies are complex and difficult for the surgeon to manipulate and install. Such polyaxial pedicle screws often have large and complex rod clamping hardware that is difficult for the surgeon to maneuver around and occupies a large portion of the surgical site.

Moreover, removal or adjustment of the pedicle screw assembly of the spinal fixation system may be required and the complex assemblies associated with known polyaxial rod clamping assemblies make such a procedure very complicated and difficult to achieve, if at all. The ability for the housing of the polyaxial pedicle screw to move relative to the remainder of the spinal fixation system provides significant advantages, but presents many difficulties when removal and/or adjustment of the rod clamping assembly is required, particularly without disrupting the pedicle screw placement in the spine. One source of some of these problems is the deformation of the pedicle screw assembly components or the spinal fixation system components when the spine rod is clamped in place. The components that remain after the spine rod and/or clamping elements is/are removed make reanimation impossible because the components are deformed during initial installation.

Room for improvement of prior art spinal fixation devices remains in the manner of reducing inventories, locking the pedicle screw components, the complexity of use, difficulty in properly positioning the orthopedic rod and the rod-capturing assemblies, the required workspace and manipulation of the many parts associated with some complex devices and the ability to remove specific components without disrupting the remainder of the spinal fixation system.

SUMMARY OF THE INVENTION

This invention addresses these and other shortcomings in the prior art. In one embodiment, the invention is a polyaxial pedicle screw with a polyaxial body which is selectively removable from the screw in a spinal fixation system without disruption of the screw's placement in the patient's spine. The polyaxial body according to various embodiments of this invention may be locked relative to the screw head and coupled to the spine rod without deformation of the screw or body components while still allowing for subsequent removal of the body from the screw head.

The removable polyaxial screw in one embodiment has a threaded shaft that is inserted into a selected vertebra of a patient. The pedicle screw also has a head with a convex portion that, in one embodiment, includes a thread extending entirely around the convex portion of the screw head. A polyaxial body is selectively engaged with the screw head and includes a U-shaped channel in which the spine rod is captured by a set screw seated in the polyaxial body. The polyaxial body and pedicle screw allow for a variety of different configurations to accommodate various patient and spine rod geometries thereby providing the polyaxial benefits associated with polyaxial pedicle screws during the installation and design of the spinal fixation system. The pedicle screw and the polyaxial body lock to each other when the spine rod is clamped by a set screw in the U-shaped channel without crimping or deforming any of the components.

In one embodiment, the head of the pedicle screw is threadably engaged with a retainer ring on the polyaxial body thereby permitting selective removal of the body from the screw head without disrupting the placement of the screw in the spine. This allows for the pedicle screw to remain in the spine as the fixation system is adjusted as required by the surgeon. The advantages of the ability to remove the polyaxial body from the polyaxial pedicle screw include reduced inventory, greater surgical work area and ease of insertion and alteration of the types of polyaxial constructs available to the surgeon when treating the patient.

The removable polyaxial pedicle screw of this invention allows for the relative motion between the polyaxial body and the pedicle screw to be locked when the spine rod is coupled thereto. The locking mechanism does not involve deformation, swaging, crimping or other mutilation of the polyaxial housing and screw components. Other locking mechanisms utilize deformation of a component or wedging a component against another and such approaches make reanimation of the polyaxial screw significantly more difficult, if possible at all.

The ability to remove the body from the installed screw offers significant benefits to the surgeon and patient. The threaded engagement between the polyaxial screw head and the polyaxial body allows for the body to be removed, replaced, adjusted and/or reattached to the screw and polyaxial construct as needed. As such, the pedicle screw insertion is not restricted by the geometry or mechanics of the polyaxial construct. Reduction in inventory is realized because a wide variety of screw configurations can be built from a few components. As an example, if five pedicle screw lengths of a specific diameter and four polyaxial body assemblies are required for a fixation system, then a total of 20 screws are currently required. With this invention, the same fixation system requirements would be satisfied with only nine components (four polyaxial bodies and five pedicle screws) thereby significantly reducing the inventory requirements for spinal fixation systems.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein.

DETAILED DESCRIPTION OF THE INVENTION

Figure 1:
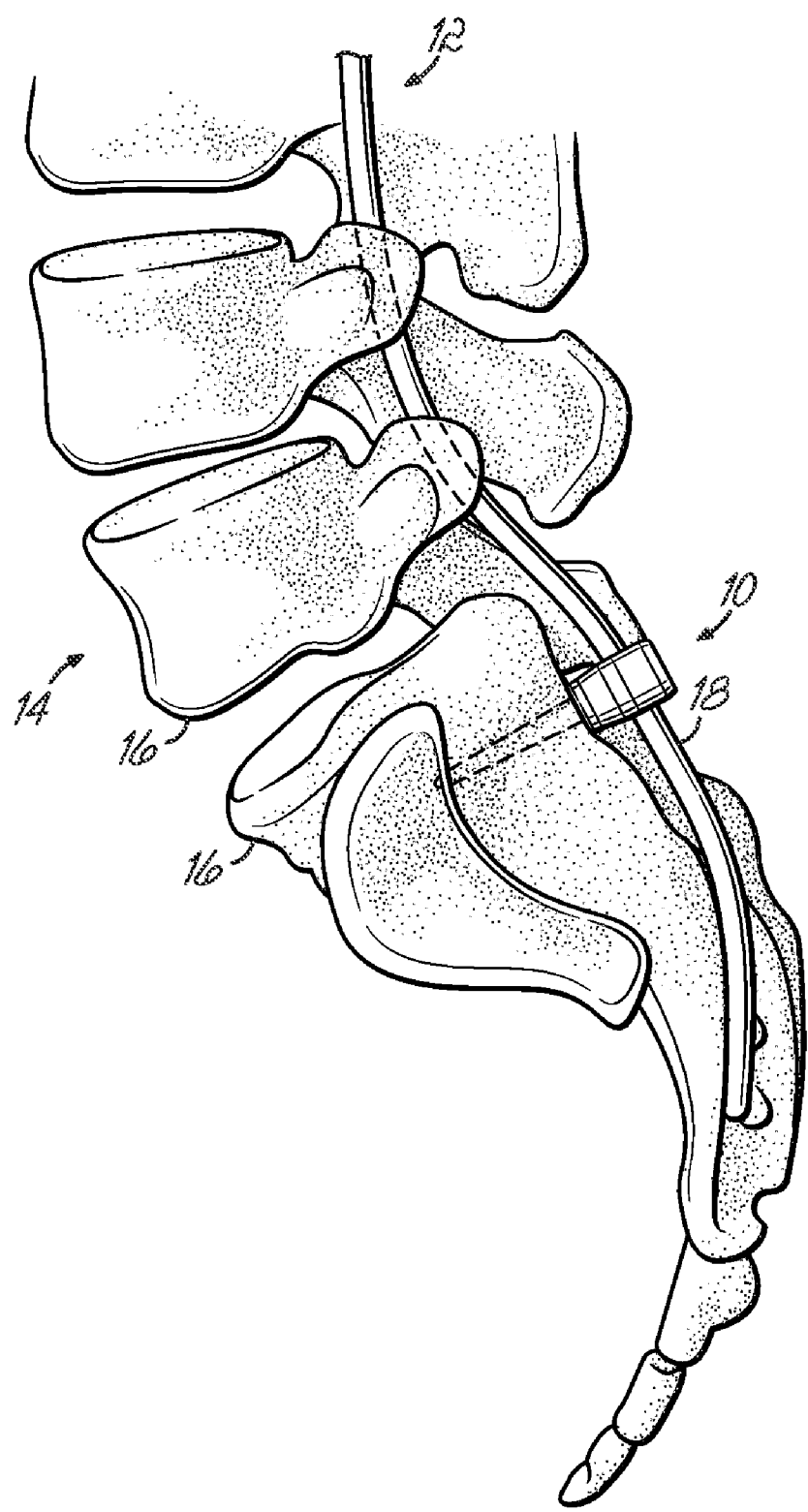
FIG. 1 is a lateral side elevation view of an exemplary spinal fixation system utilizing a pedicle screw according to one embodiment of this invention.

Referring to FIG. 1, one embodiment of a removable polyaxial pedicle screw assembly 10 is shown as part of a spinal fixation system 12 mounted to a spine 14 of a patient. The pedicle screw assembly 10 is shown inserted into a vertebra 16 in the sacrum of the patient's spine 14 with a spine rod 18 mounted to the pedicle screw assembly 10. However, it will readily be appreciated by those of ordinary skill in the art that the pedicle screw of this invention can readily be used at other locations along the spine or other bones in a patient's body in addition to those shown in FIG. 1.

Figure 2:
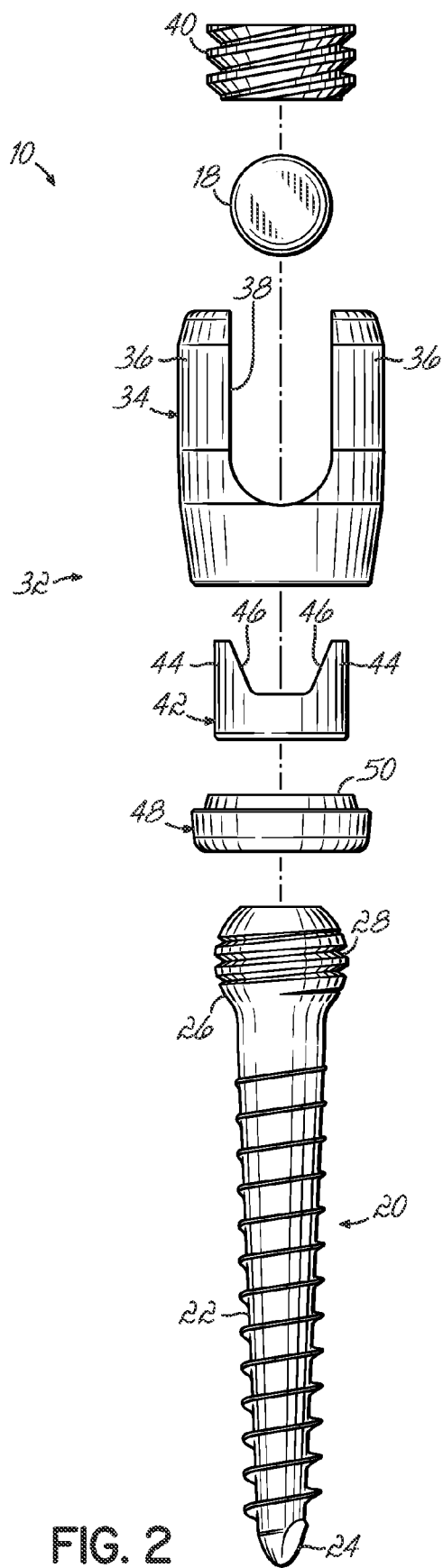
FIG. 2 is a side elevational view of the components of a pedicle screw assembly according to one embodiment of this invention.

As shown in FIG. 2, the pedicle screw assembly 10 according to one embodiment of this invention includes a pedicle screw 20 having a threaded shaft 22 and a tip 24 for insertion into the spine 14. A head 26 of the screw 20 is located opposite from the tip 24 and includes a generally spherical or convex profile with a helical thread 28 extending circumferentially around the screw head 26. The pedicle screw 20 includes a hexagonal or other shaped socket 30 (FIG. 4) by which an appropriate tool may be utilized by a surgeon to screw the pedicle screw 20 into the patient's spine 14 or other bone structure.

Figure 3:
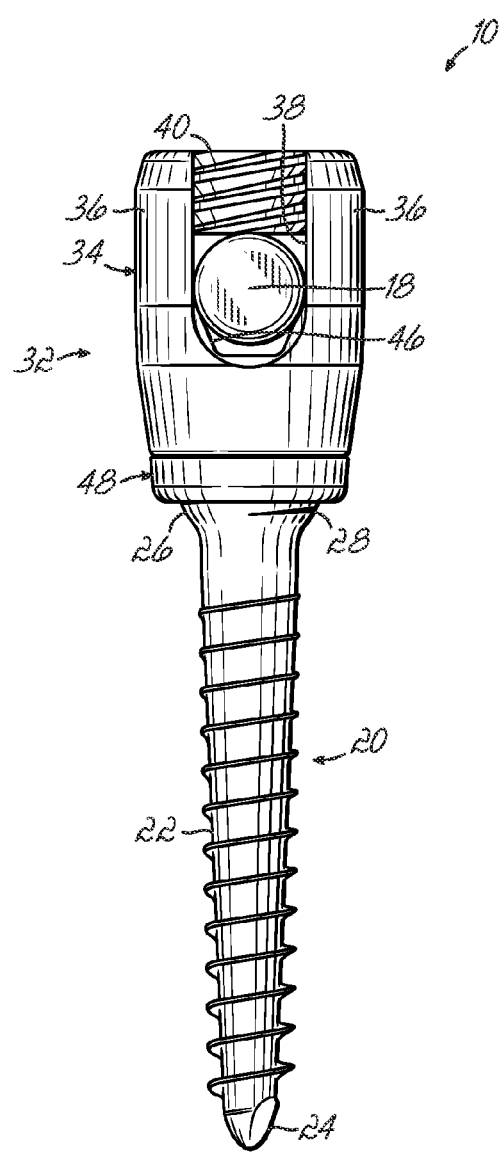
FIG. 3 is a view similar to FIG. 2 with the components in an assembled configuration.
Figure 5:
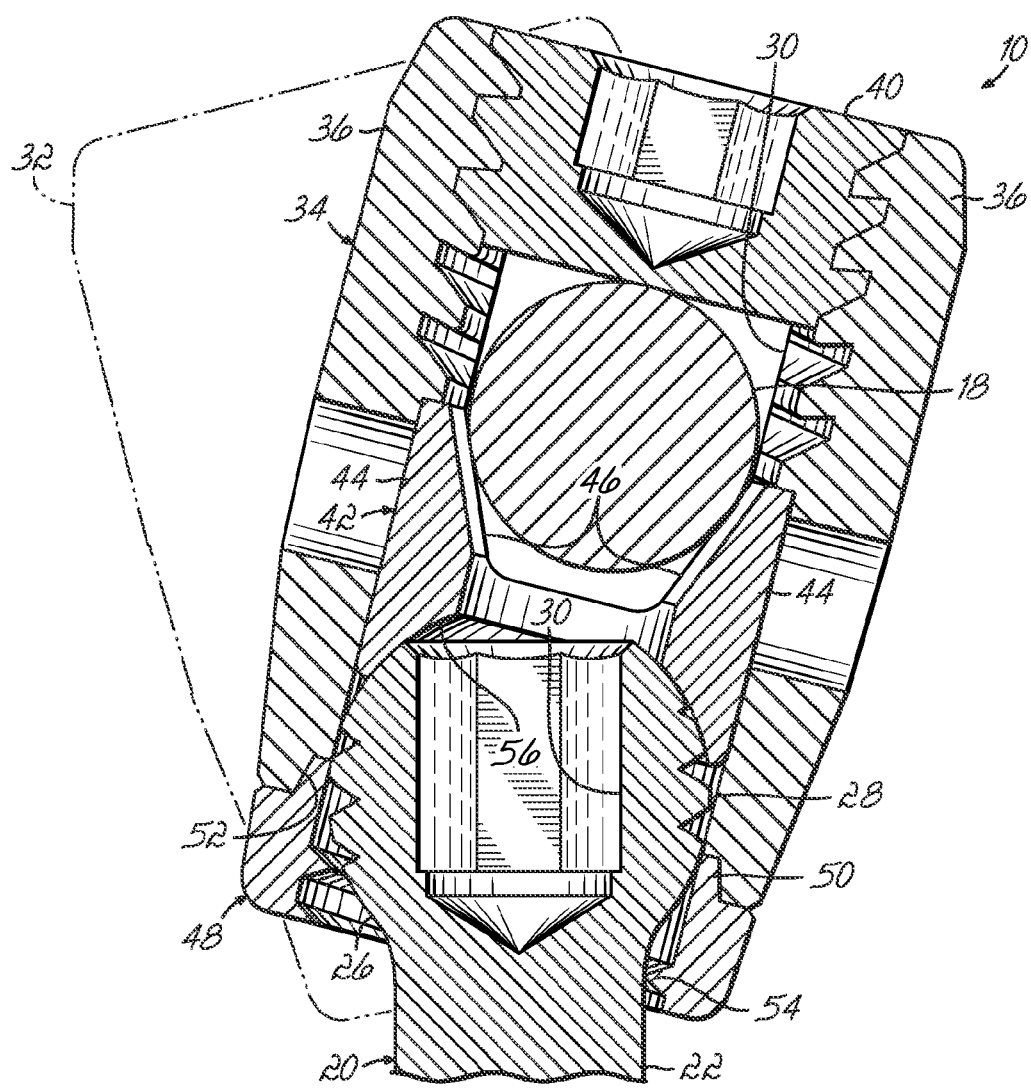
FIG. 5 is a cross-sectional view with the head of the pedicle screw locked relative to the polyaxial body by the rod and set screw in the U-shaped channel of the polyaxial body.

A polyaxial body 32 may be selectively mounted to the pedicle screw 20 according to various embodiments of this invention. The polyaxial housing 32 includes a polyaxial housing 34 having a pair of opposed upwardly directed and spaced arms 36 forming a generally U-shaped channel 38. The U-shaped channel 38 of the polyaxial housing receives the spine rod 18 seated therein. The spine rod 18 is captured in the U-shaped channel 38 by a set screw 40 which is threadably engaged between the upstanding arms 36 of the polyaxial housing 34 as shown in FIGS. 3 and 5. The polyaxial housing includes a longitudinal bore hole there through.

The polyaxial body 32 also includes a cylindrical bushing 42 with a pair of upstanding flanges 44 having confronting angular faces 46. The polyaxial body 32 also includes a retainer ring 48 seated on a distal end of the polyaxial head 34 opposite from the U-shaped channel 38. The retainer ring 48 includes an upwardly directed annular flange 50 which is sized and configured to mate within an annular rim 52 formed in the bottom end of the polyaxial housing 34. The bushing 42 and retainer ring 48 each also have a central longitudinal bore extending there through. The retainer ring 48 has an internal thread 54 formed on an inner circumference thereof around the bore which is designed and configured to threadably engage with the thread 28 on the head 26 of the pedicle screw 20 as will be described later herein.

Figure 4:
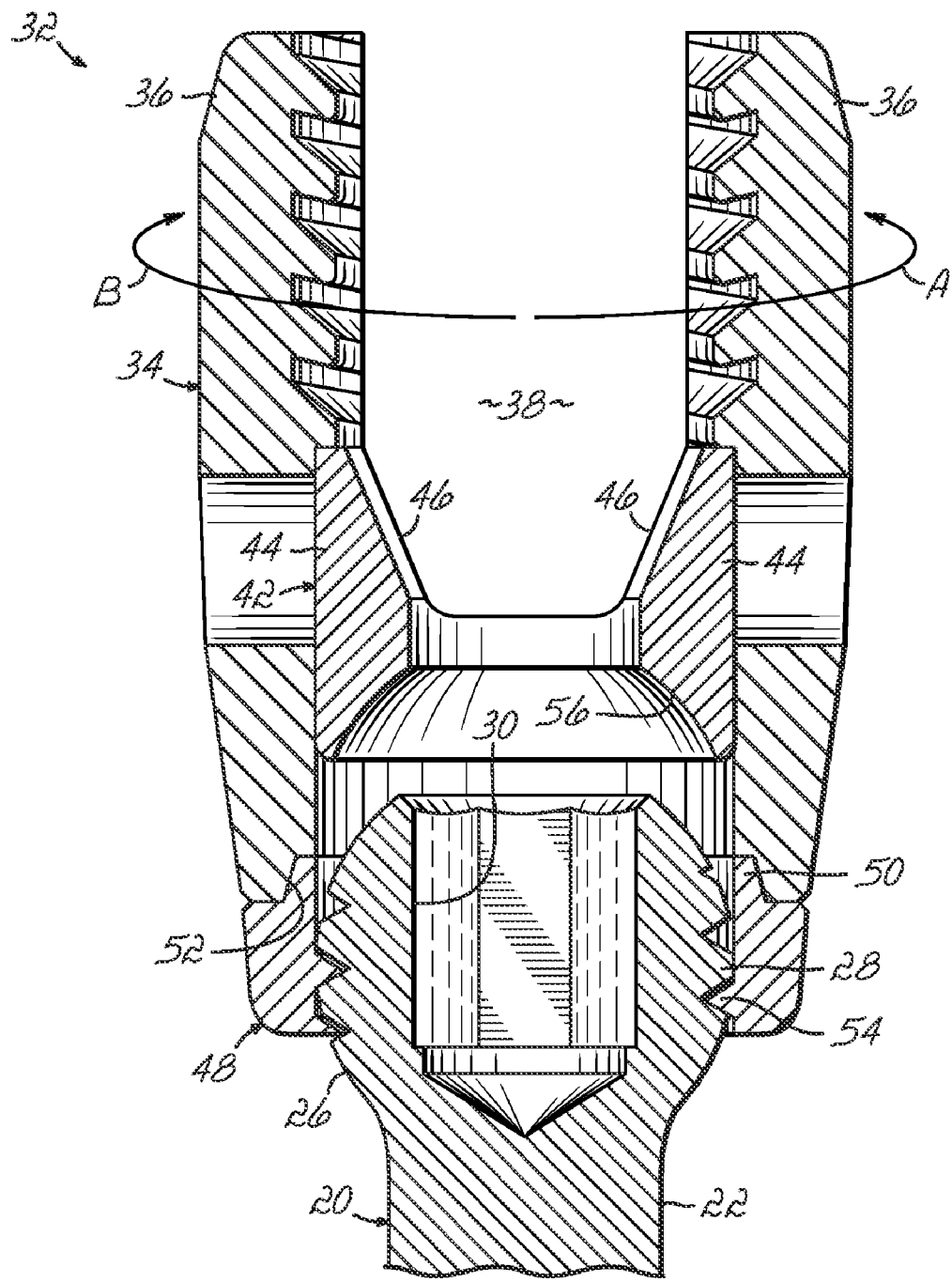
FIG. 4 is a cross-sectional view of a polyaxial body of the pedicle screw assembly being rotated relative to the polyaxial screw head.

The outer circumference of the bushing 42 is sized and configured to seat within the longitudinal bore of the polyaxial housing 34 as shown generally in FIGS. 4 and 5. The bushing 42 also includes a concave-shaped seat 56 on a bottom end thereof opposite from the upwardly directed angular flanges 44. The concave-shaped seat 56 in the bushing 42 is sized and configured to mate with the upper convex portion of the pedicle screw head 26 as will be described later herein.

The polyaxial body 32 is capable of pivotal, rotational and angular movement relative to the pedicle screw 20 to allow a surgeon the ability to position the pedicle screw 20 in the patient's spine 14 securely while still accommodating the various geometries and contours of the spine rod 18 as shown in FIG. 5. The polyaxial pedicle screw 20 benefits are well known in the art and these benefits are likewise realized by this invention. Additional advantages offered by the pedicle screw assembly 10 of this invention are also realized. For example, once the proper orientation of the polyaxial body 32 relative to the pedicle screw 20 is obtained, the rod 18 is forced downwardly in the U-shaped channel 38 by the set screw 40. The downward pressure of the rod 18 and set screw 40 on the bushing 42 forces the concave seat 56 of the bushing 42 downwardly onto the mating convex portion of the pedicle screw head 26 thereby locking the position of the polyaxial body 32 relative to the pedicle screw 20. The spine rod 18 is seated on the angled faces 46 of the bushing flanges 44 and the bushing 42 is forced downwardly onto the head 26 of the pedicle screw 20 in the relative orientation desired by the surgeon. Advantageously, the polyaxial body 32 and pedicle screw 20 are fixed or locked relative to one another without deformation of any of the components of the pedicle screw assembly 10 unlike prior polyaxial pedicle screw arrangements.

In the event that the surgeon wishes to adjust, replace or modify specific components or otherwise service the spinal fixation construct 12, such procedures can be accomplished without removal of the pedicle screw 20 from the patient's spine 14 with this invention. Specifically, once the spine rod 18 and set screw 40 are removed from the polyaxial body 32, the polyaxial body 32 can be unscrewed from the head 26 of the pedicle screw 20 as shown generally by arrow A in FIG. 4. Then the same or a different polyaxial body 32 having a thread 54 compatible with the thread 28 on the head 26 of the pedicle screw 20 may be reinstalled onto the pedicle screw 20 while the pedicle screw 20 remains securely installed in the patient's spine 14. The threaded engagement between the head 26 of the pedicle screw 20 and the polyaxial body 32 is not engaged during normal operation of the spinal fixation construct as shown generally in FIG. 5. However, once the spine rod 18 and set screw 40 are removed from the channel 38 of the polyaxial housing 34, the bushing 42 is free to disengage from the head 26 of the pedicle screw 20 and adjustment of the polyaxial body 32 relative to the pedicle screw 20 may be accomplished. Additionally, the polyaxial body 32 according to this invention may be selectively installed on the pedicle screw 20 as shown by arrow B. The polyaxial body 32 may be selectively installed, removed and reinstalled on the pedicle screw 20 through the threaded engagement between the retainer ring 48 and the pedicle screw head 26. As such, the polyaxial body 32 can be assembled to and removed from the pedicle screw 20 as required by the surgeon thereby affording increased access at the surgical site in the absence of the polyaxial housing 32 which, in many cases with the prior art designs, block and obstructed surgeon access.

The polyaxial motion of the polyaxial body 32 with respect to the pedicle screw 20 is locked by transferring the load from the set screw 40 through the spine rod 18 to the bushing 42 and onto the head 26 of the pedicle screw 20. The pedicle screw head 26 is captured between the bushing 42 and the retainer ring 48. The retainer ring 48 may be welded onto the distal end of the polyaxial housing 34. Meanwhile, all these advantages are achieved through this invention while providing for selective removal and installation of the polyaxial body 32 onto the head 26 of the pedicle screw 20 through the threaded engagement between the retainer ring 48 and the screw head 26.

From the above disclosure of the general principles of the present invention and the preceding detailed description of at least one preferred embodiment, those skilled in the art will readily comprehend the various modifications to which this invention is susceptible. Therefore, I desire to be limited only by the scope of the following claims and equivalents thereof.

I claim:

1. A pedicle screw assembly comprising:
    a screw having a threaded shaft and a head including a threaded convex portion;
    a polyaxial body coupled to the screw and having a channel proximate a first end of the body adapted to receive a spine rod therein and a longitudinal bore extending into the body from a second end of the body, an angular orientation of the screw relative to the body being adjustable in a first configuration;
    a retainer ring mounted on edge of the second end of the polyaxial body spaced from the first end of the body, the retainer ring including a threaded opening extending through the retainer ring; and
    a bushing captured in the longitudinal bore of the body intermediate the channel and the retainer ring, the bushing being positioned in the longitudinal bore of the body from the second end of the body wherein the bushing is sized to be positioned within the longitudinal bore prior to the retainer ring being fixedly mounted on the edge of the second end of the polyaxial body and is not removable from the longitudinal bore after the retainer ring is fixedly mounted on the edge of the second end of the polyaxial body;
    wherein the threaded convex portion of the head of the screw is sized to be threadably advanced through the threaded opening of the retainer ring;
    wherein the screw is selectively coupled to the body by passing the head through the threaded opening of the retainer ring to position the head between the bushing and the retainer ring, the body being selectively removable from the screw by passing the screw head through the threaded opening of the retainer ring;
    wherein the body is fixed relative to the screw head in a second configuration when the spine rod forces the bushing onto the screw head;
    wherein in a first assembly position in which the screw is coupled to the body, the screw extends through the opening of the retainer ring with the threaded convex portion of the head of the screw not threadedly engaged with the threaded opening of the retainer ring, and
    wherein in a second assembly position in which the screw is coupled to the body, the threaded convex portion of the head of the screw is threadedly engaged with the threaded opening of the retainer ring.

2. The pedicle screw assembly of claim 1 the bushing includes a concave seat, the convex portion of the head of the screw being seated in the concave seat in the second configuration to inhibit the relative movement between the screw and the body.

3. The pedicle screw assembly of claim 1 wherein the body further comprises:
    a set screw threadably engaged with the body to capture the spine rod in the channel and force the bushing onto the screw head to thereby inhibit angular motion of the screw relative to the body in the second configuration.

4. The pedicle screw assembly of claim 1 wherein the retainer ring is spaced from the bushing in the body.

5. The pedicle screw assembly of claim 1 wherein a longitudinal axis of the screw shaft is aligned with a longitudinal axis of the body when the screw head is passing through the retainer ring.

6. The pedicle screw assembly of claim 1 wherein the retainer ring includes an annular flange which mates within an annular rim formed in the second end of the body.

7. The pedicle screw assembly of claim 1 wherein the bushing is not removable from the body through the first end of the body.

8. A pedicle screw assembly comprising:
a screw having a head including a threaded portion and a shaft extending from the head to a tip of the screw, the shaft having a threaded portion and a non-threaded portion between the head and the threaded portion of the shaft;
a polyaxial body coupled to the screw and having a channel proximate a first end of the body adapted to receive a spine rod therein, an angular orientation of the screw relative to the body being adjustable in a first configuration;
a retainer ring fixedly mounted to the polyaxial body on edge of a second end of the body spaced from the first end, the retainer ring including a threaded opening extending through the retainer ring;
a bushing captured in the body intermediate the channel and the retainer ring; and
a set screw threadably engaged with the body to capture the spine rod in the channel and force the bushing onto the screw head to thereby inhibit angular motion of the screw relative to the body in a second configuration;
wherein the screw is selectively coupled to the body by passing the head through the retainer ring to position the head between the bushing and the retainer ring with the retainer ring surrounding the non-threaded portion of the shaft and not threadably engaged with the threaded portion of the head such that the body is fixed relative to the screw head in the second configuration, the body being selectively removable from the screw by passing the screw head through the retainer ring;
wherein the threaded portion of the head of the screw is sized to be threadably advanced through the threaded opening of the retainer ring; and
wherein the threaded portion of the head of the screw and the threaded opening of the retainer ring provide a threaded engagement between the screw head and the retainer ring to permit selective insertion and selective removal of the screw head from the body;
wherein the bushing is sized to be secured between the channel and the retainer ring when the retainer ring is mounted to the polyaxial body and removable from the second end of the body when the retainer ring is not mounted to the body.

9. The pedicle screw assembly of claim 8 wherein the screw head includes a convex portion and the bushing includes a concave seat, the convex portion being seated in the concave seat to inhibit the relative movement between the screw and the body in the second configuration.

10. A spinal fixation system comprising:
a plurality of pedicle screws adapted to be inserted into selected vertebrae of a spine of a patient;
a spine rod configured to extend along a portion of the spine and being connected with each of the pedicle screws;
wherein at least one of the pedicle screws further comprises,
(a) a threaded shaft and a head including a threaded convex portion;
(b) a polyaxial body adapted to be coupled to the at least one pedicle screw and having a channel proximate a first end of the body and adapted to receive the spine rod therein, an angular orientation of the at least one pedicle screw relative to the body being adjustable in a first configuration;
(c) a retainer ring fixedly secured to the polyaxial body on edge of a second end of the body spaced from the first end, the retainer ring including a threaded opening extending through the retainer ring, the threaded opening of the retainer ring being sized to allow the threaded convex portion of the head of the screw to be threadably advanced through the threaded opening; and
(d) a bushing captured in a housing intermediate the channel and the retainer ring;
wherein the at least one pedicle screw is selectively coupled to the body by threadably inserting the threaded convex portion of the head of the screw through the threaded opening of the retainer ring to position the head between the bushing and the retainer ring such that the body is fixed relative to the screw head in a second configuration when the spine rod forces the bushing onto the screw head, the body being selectively removable from the screw by threadably removing the threaded convex portion of the head of the screw through the threaded opening of the retainer ring;
wherein the bushing is sized to be removable from the housing prior to fixedly securing the retainer ring to the polyaxial body and to be secured within the housing when the retainer ring is fixedly secured to the polyaxial body.

11. The system of claim 10 wherein the bushing includes a concave seat, the threaded convex portion of the head of the screw being seated in the concave seat in the second configuration.

12. The system of claim 10 wherein the housing further comprises:
a set screw threadably engaged with the body to capture the spine rod in the channel and force the bushing onto the screw head to thereby inhibit angular motion of the at least one pedicle screw relative to the body.

* * * * *

UNITED STATES PATENT AND TRADEMARK OFFICE
CERTIFICATE OF CORRECTION

| | | |
|---|---|---|
| PATENT NO. | : 7,922,748 B2 | Page 1 of 1 |
| APPLICATION NO. | : 11/424562 | |
| DATED | : April 12, 2011 | |
| INVENTOR(S) | : Zachary M. Hoffman | |

It is certified that error appears in the above-identified patent and that said Letters Patent is hereby corrected as shown below:

Column 6
Line 19, after "ring", insert -- fixedly --

Signed and Sealed this
Twenty-eighth Day of June, 2011

David J. Kappos
*Director of the United States Patent and Trademark Office*